United States Patent
Wang et al.

(10) Patent No.: US 10,076,366 B2
(45) Date of Patent: Sep. 18, 2018

(54) VERTEBRAL LAMINA SUPPORTING DEVICE

(71) Applicant: ESSENCE MEDICAL DEVICES CO., LTD., Taichung (TW)

(72) Inventors: Hung-Chen Wang, Taichung (TW); Hung-Ku Lin, Taichung (TW)

(73) Assignee: ESSENCE MEDICAL DEVICES CO., LTD., Taichung (TW)

( * ) Notice: Subject to any disclaimer, the term of this patent is extended or adjusted under 35 U.S.C. 154(b) by 0 days.

(21) Appl. No.: 15/657,204

(22) Filed: Jul. 23, 2017

(65) Prior Publication Data

US 2018/0110549 A1    Apr. 26, 2018

(30) Foreign Application Priority Data

Oct. 21, 2016   (TW) .............................. 105134158 A
Feb. 22, 2017   (CN) .......................... 2017 1 0096288

(51) Int. Cl.
*A61B 17/70* (2006.01)
*A61F 2/44* (2006.01)

(52) U.S. Cl.
CPC .......... *A61B 17/7062* (2013.01); *A61B 17/70* (2013.01); *A61B 17/7055* (2013.01); *A61B 17/7064* (2013.01); *A61B 17/7071* (2013.01); *A61F 2/44* (2013.01); *A61F 2002/4435* (2013.01)

(58) Field of Classification Search
CPC . A61B 17/7062; A61B 17/70; A61B 17/7064; A61F 2/44; A61F 2002/4435
USPC ..................... 606/248, 249; 623/17.15, 17.16
See application file for complete search history.

(56) References Cited

U.S. PATENT DOCUMENTS

| | | | |
|---|---|---|---|
| 5,733,284 A | 3/1998 | Fairant | |
| 8,267,970 B2 * | 9/2012 | Serhan | A61B 17/7071 600/236 |
| 8,470,000 B2 * | 6/2013 | Trautwein | A61B 17/7049 606/249 |

(Continued)

FOREIGN PATENT DOCUMENTS

| | | |
|---|---|---|
| CN | 101422387 A | 5/2009 |
| CN | 204521061 U | 8/2015 |
| TW | M466634 U | 12/2013 |

*Primary Examiner* — Pedro Philogene
*Assistant Examiner* — David C Comstock
(74) *Attorney, Agent, or Firm* — CKC & Partners Co., Ltd.

(57) ABSTRACT

A vertebral lamina supporting device is provided. The vertebral lamina supporting device includes a first supporting member, a second supporting member and at least one connecting member. The first supporting member includes a first supporting base, in which the first supporting base has a first abutting surface and a first surface opposite to the first abutting surface. The first abutting surface has at least two radially arranged first concave arc portions. The second supporting member is movable relative to the first supporting member. The second supporting member includes a second supporting base, in which the second supporting base has a second abutting surface and a second surface opposite to the second abutting surface. The second abutting surface has at least two radially arranged second concave arc portions. The connecting member is connected between the first supporting member and the second supporting member.

16 Claims, 17 Drawing Sheets

(56) References Cited

U.S. PATENT DOCUMENTS

| | | | |
|---|---|---|---|
| 2007/0270827 A1* | 11/2007 | Lim ................... | A61B 17/7062 606/86 A |
| 2009/0292314 A1* | 11/2009 | Mangione .......... | A61B 17/7062 606/249 |
| 2011/0218572 A1* | 9/2011 | Lechmann ......... | A61B 17/7062 606/249 |
| 2014/0025114 A1* | 1/2014 | Kim ................... | A61B 17/7062 606/249 |
| 2014/0107704 A1* | 4/2014 | Serhan ............... | A61B 17/7062 606/249 |

* cited by examiner

VERTEBRAL LAMINA SUPPORTING DEVICE

RELATED APPLICATIONS

This application claims priority to Taiwan Application Serial Number 105134158, filed on Oct. 21, 2016, and China Application Serial Number 201710096288.0, filed on Feb. 22, 2017, which are incorporated herein by reference.

BACKGROUND

Field of Invention

The present invention relates to a vertebral lamina supporting device. More particularly, the present invention relates to a vertebral lamina supporting device which can be used to abut against vertebral laminas of the vertebrae.

Description of Related Art

Referring to FIG. 1 and FIG. 2, FIG. 1 and FIG. 2 are schematic diagrams showing a conventional spinous process device 80 in use. The human spine includes individual vertebrae 90 that interlock with each other to form a spinal column. Each vertebra mainly includes a vertebral body 91, a lamina 92 and a spinous process 93 extending from the lamina 92. The conventional spinous process device 80 is mainly used to be disposed between two adjacent spinous process 93 to reduce the oppressive force on vertebral nerve. Furthermore, the conventional spinous process device 80 is used to support the two adjacent spinous process 93 to release the oppressive force on vertebral nerve.

As shown in FIG. 1 and FIG. 2, the conventional spinous process device 80 includes a main body 81. The main body 81 has two abutting portions 81a disposed on two opposite ends of the main body 81. Therefore, when the conventional spinous process device 80 is disposed between the two adjacent vertebrae 90, the abutting portions 81a respectively abut against the two adjacent spinous processes 93 of the vertebrae 90.

Simultaneously referring to FIG. 3, FIG. 3 is a schematic diagram showing a relative position between the vertebrae and the conventional spinous process device 80. However, when the abutting portions 81a of the conventional spinous process device 80 abut against the spinous processes 93, supporting force provided by the abutting portions 81a is mainly concentrated on the spinous processes 93. Because the spinous processes 93 are thinner parts of the vertebrae 90, when the spinous processes 93 are continuously under forced, the spinous processes 93 will be fractured (a fractured portion 910a is shown in FIG. 3).

On the other hand, because the conventional spinous process device 80 needs to be disposed on the spinous processes, and the sacral vertebrae of human body does not have adequate spinous processes, the conventional spinous process device 80 cannot be placed between the spinous processes of last lumbar vertebrae and the top portion of sacral vertebrae.

SUMMARY

An object of the invention is to provide a vertebral lamina supporting device which can be used to solve the fracture problem of spinous processes caused by the conventional spinous process device.

According to the aforementioned object, a vertebral lamina supporting device is provided. The vertebral lamina supporting device includes a first supporting member, a second supporting member and at least one connecting member. The first supporting member includes a first supporting base, in which the first supporting base has a first abutting surface and a first surface opposite to the first abutting surface. The first abutting surface has at least two radially arranged first concave arc portions. The second supporting member is movable relative to the first supporting member. The second supporting member includes a second supporting base, in which the second supporting base has a second abutting surface and a second surface opposite to the second abutting surface. The second abutting surface has at least two radially arranged second concave arc portions. The connecting member is connected between the first supporting member and the second supporting member.

According to an embodiment of the present invention, the first supporting member comprises a first supporting post disposed on the first surface. The second supporting member comprises a second supporting post disposed on the second surface.

According to an embodiment of the present invention, the connecting member is a fixing member, and the fixing member is configured to be inserted into and fixed on the first supporting post and the second supporting post.

According to an embodiment of the present invention, the first supporting post has at least one first fixing hole. The second supporting post has at least one second fixing hole corresponding to the first fixing hole.

According to an embodiment of the present invention, the vertebral lamina supporting device further includes a sleeve. The sleeve is put around the second supporting post and the first supporting post.

According to an embodiment of the present invention, the first supporting post has at least one first fixing hole. The second supporting post has at least one second fixing hole corresponding to the first fixing hole, and each of the first fixing hole and the second fixing hole is a through hole. The sleeve has at least one first threaded hole corresponding to the first fixing hole and the second fixing hole. The fixing member has a threaded portion, and the fixing member is inserted into the first threaded hole, the second fixing hole and the first fixing hole, and the threaded portion of the fixing member is screwed in the first threaded hole.

According to an embodiment of the present invention, the fixing member further includes a head portion, and the head portion and the threaded portion are respectively disposed on two opposite ends of the fixing member. The sleeve further includes at least one second threaded hole, and the second threaded hole and the first threaded hole are respectively located on two opposite sides of the sleeve, and the head portion is located in the second threaded hole.

According to an embodiment of the present invention, the vertebral lamina supporting device further includes at least one nut, in which the nut is screwed in the second threaded hole and abuts against the head portion of the fixing member.

According to an embodiment of the present invention, each surface of each of the first supporting post, the second supporting post and the sleeve has a convex arc surface and a concave arc surface.

According to an embodiment of the present invention, the sleeve has a large opening and a small opening opposite to each other, and the sleeve has a flange surrounding the small opening, in which a bottom surface of the second supporting post abuts against the flange.

According to an embodiment of the present invention, the connecting member is an elastic member disposed between the first supporting post and the second supporting post.

According to an embodiment of the present invention, the elastic member is located in the second supporting post and abuts against a top surface of the first supporting post.

According to an embodiment of the present invention, the elastic member surrounds the first supporting post and the second supporting post, and one end of the elastic member abuts against the first surface of the first supporting base, and the other end of the elastic member abuts against the second surface of the second supporting base.

According to an embodiment of the present invention, the connecting member is an elastic member disposed between the first supporting member and the second supporting member.

According to an embodiment of the present invention, the first supporting member, the second supporting member and the connecting member are integrally formed.

According to an embodiment of the present invention, the first supporting member, elastic member is a C-shaped structure.

According to the aforementioned embodiments of the present invention, the relative position between the first supporting member and the second supporting member can be adjusted to change a gap between the two adjacent vertebrae and to steadily support the two adjacent vertebrae. In addition, each of the first abutting surface and the second abutting surface of the vertebral lamina supporting device has the concave arc surfaces which can abut against the triangle area between the vertebral lamina and the spinous process of the vertebrae, such that the supporting surface is increased, thereby preventing the spinous process from being fractured due to too much force applied on the spinous process.

In addition, the cross section of each sleeve, the first supporting member and the second supporting member is in a shape which has a convex side and a concave side opposite to the convex side, and the concave side faces the inner side of the vertebrae, thereby preventing the nerve from being oppressed when the vertebral lamina supporting device is disposed on the vertebrae.

BRIEF DESCRIPTION OF THE DRAWINGS

The invention can be more fully understood by reading the following detailed description of the embodiment, with reference made to the accompanying drawings as follows.

DETAILED DESCRIPTION

Figure 4:
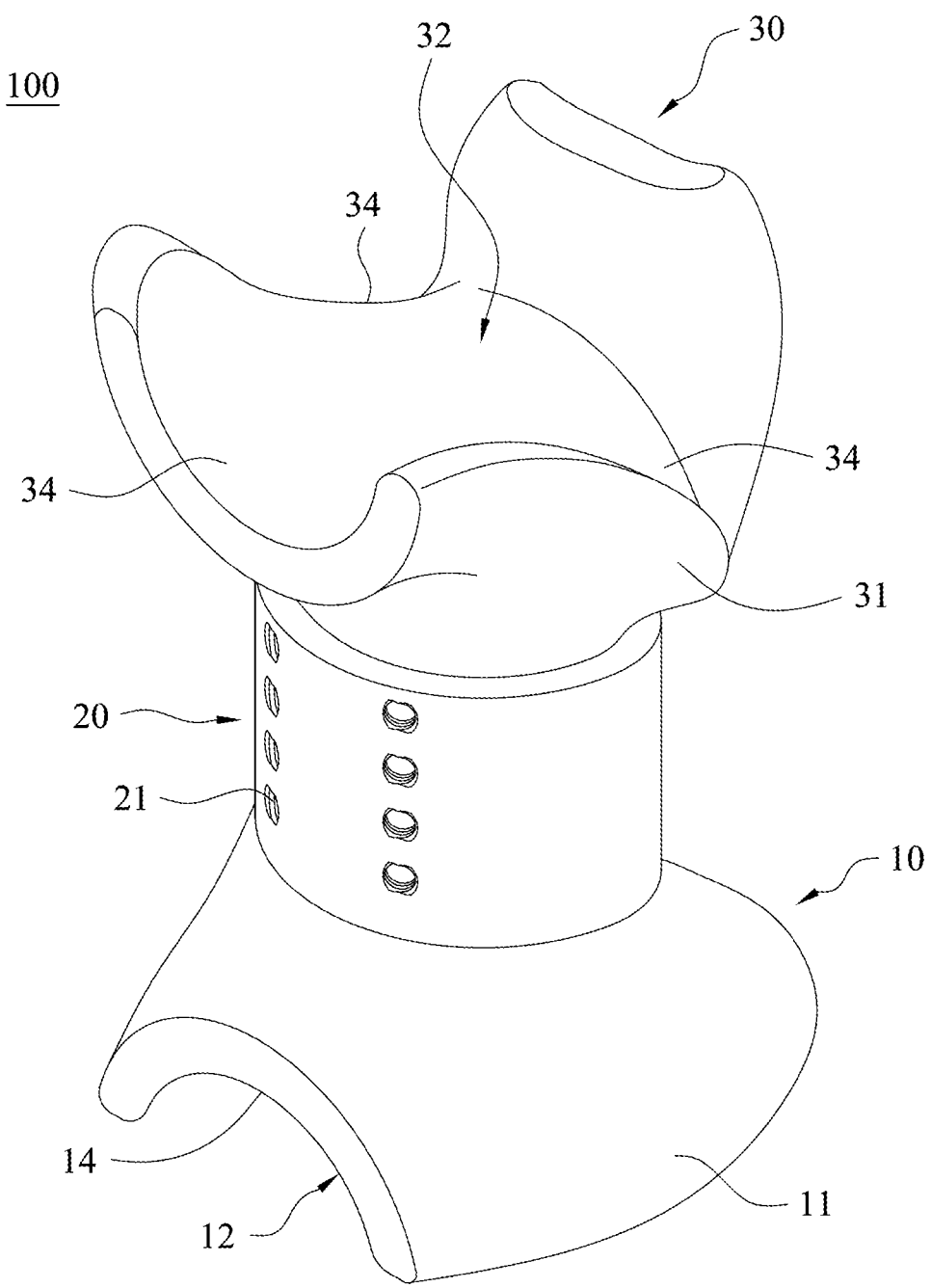
FIG. 4 is a schematic structural diagram showing a vertebral lamina supporting device in accordance with a first embodiment of the present invention.
Figure 5:
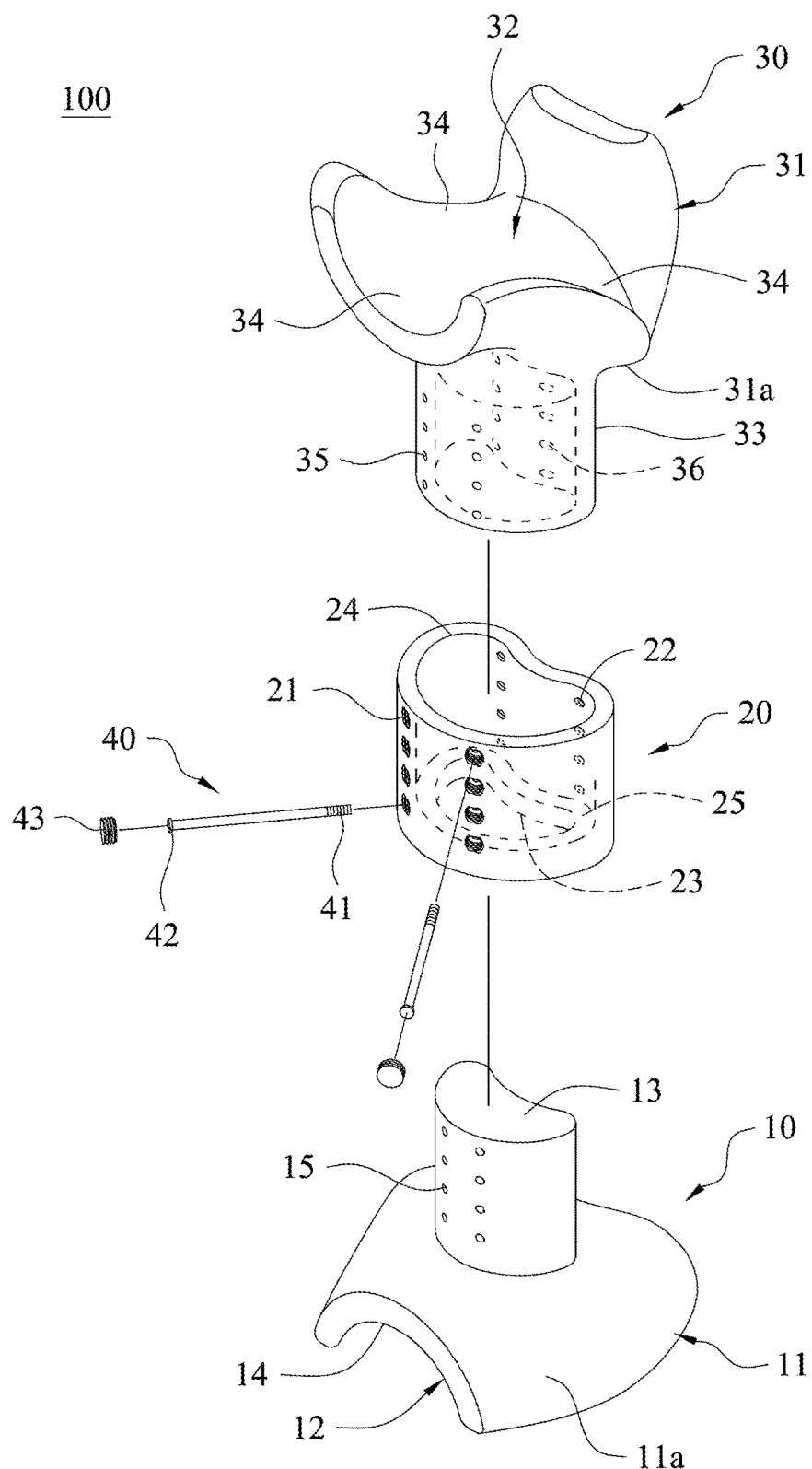
FIG. 5 is a schematic exploded view of the vertebral lamina supporting device in accordance with the first embodiment of the present invention.

Simultaneously referring to FIG. 4 and FIG. 5, FIG. 4 is a schematic structural diagram showing a vertebral lamina supporting device 100 in accordance with a first embodiment of the present invention, and FIG. 5 is a schematic exploded view of the vertebral lamina supporting device 100 in accordance with the embodiment of the first present invention. The vertebral lamina supporting device 100 mainly includes a first supporting member 10, a sleeve 20, a second supporting member 30 and at least one connecting member 40. In the present embodiment, the connecting member 40 is a fixing member 40.

Figure 11:
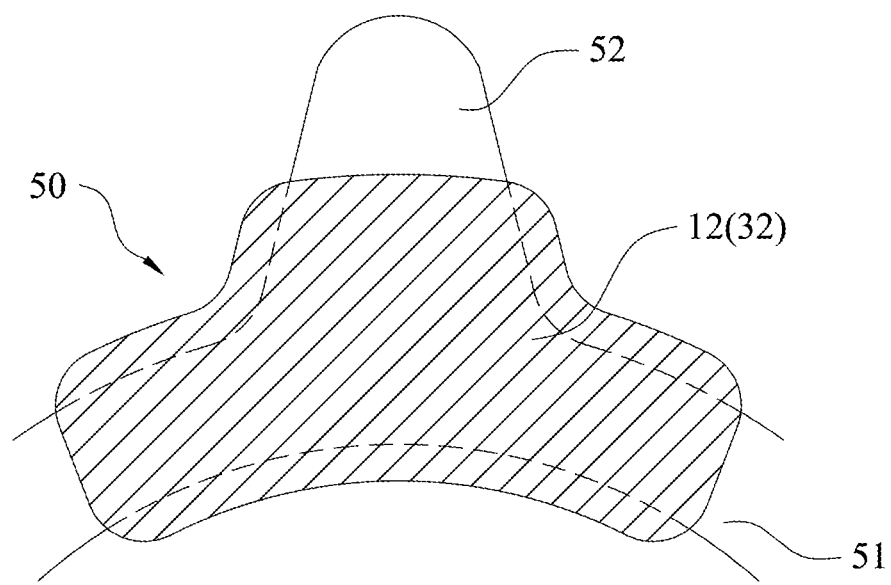
FIG. 11 is a schematic diagram showing a relative position between a vertebra and the vertebral lamina supporting device in accordance with the first embodiment of the present invention.

Referring to FIG. 4 and FIG. 5 again, the first supporting member 10 includes a first supporting base 11 and a first supporting post 13. The first supporting base 11 has a first surface 11a and a first abutting surface 12 opposite to each other, and the first supporting post 13 is disposed on the first surface 11a. In the present embodiment, the first abutting surface 12 is mainly used to abut against the vertebral lamina 51 of the vertebrae 50 (as shown in FIG. 11). In one embodiment, the first abutting surface 12 has at least two first concave arc portions 14. In one example, the first abutting surface 12 has three radially arranged first concave arc portions 14 respectively contacting a triangle area between the vertebral lamina 51 and the spinous process 52 of the vertebrae 50 (as shown in FIG. 11). In some examples, the arc surface of the first abutting surface 12 can be designed according to the radians of the patients' vertebral laminas 51, in which the radians of the vertebral laminas 51 can be obtained by computed tomography scanning.

Figure 6:
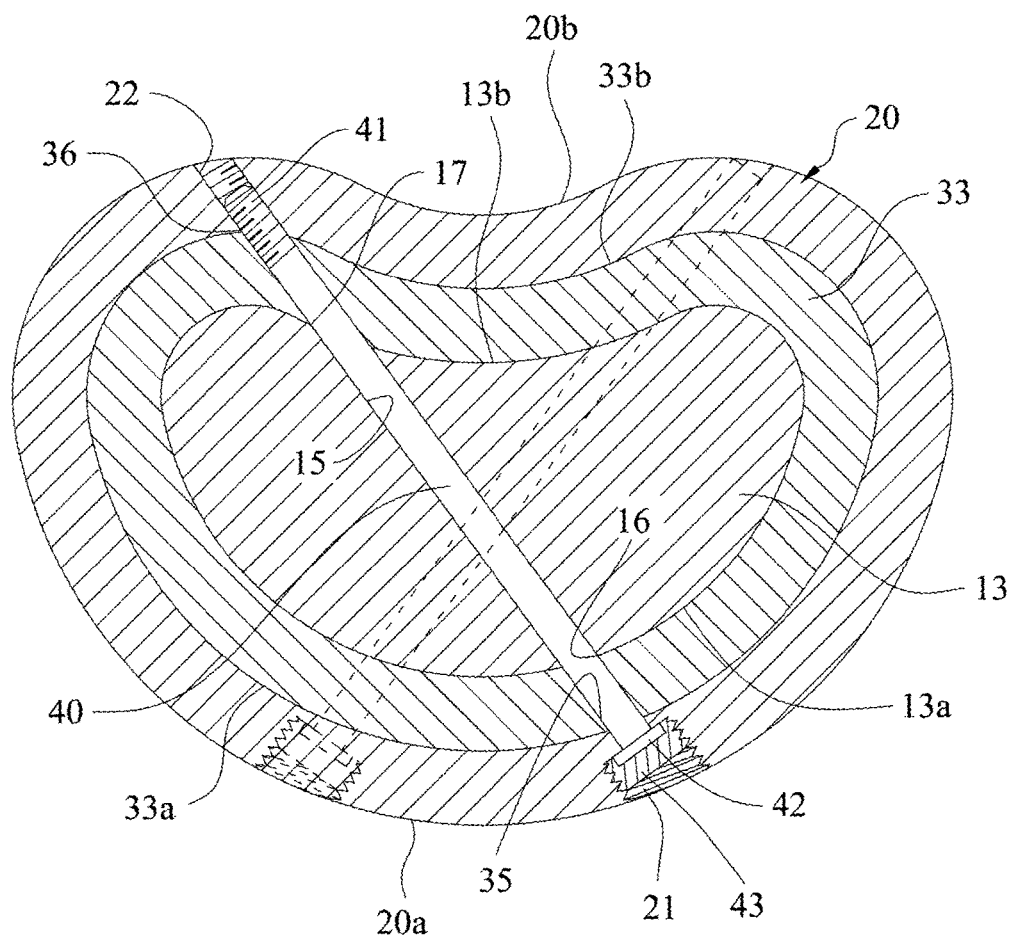
FIG. 6 is a cross-sectional view showing the vertebral lamina supporting device in accordance with the first embodiment of the present invention.

Simultaneously referring to FIG. 5 and FIG. 6, in which FIG. 6 is a cross-sectional view showing the vertebral lamina supporting device 100 in accordance with the first embodiment of the present invention. In the present embodiment, the first supporting post 13 is a solid structure. An outer surface of the first supporting post 13 includes a convex arc surface 13a and a concave arc surface 13b opposite to each other. In addition, the first supporting post 13 has plural first fixing holes 15. These first fixing holes 15 penetrate from the convex arc surface 13a to the concave arc surface 13b of the first supporting post 13, and an opening 16 and an opening 17 are respectively formed on the convex arc surface 13a and the concave arc surface 13b. In one example, the first fixing holes 15 are arranged at intervals.

Referring to FIG. 4 and FIG. 5 again, the second supporting member 30 includes a second supporting base 31 and a second supporting post 33. The second supporting base 31 has a second surface 31a and a second abutting surface 32 opposite to each other, and the second supporting post 33 is disposed on the second surface 31a. In the present embodiment, the second abutting surface 32 is mainly used to abut against the vertebral lamina 51 of the vertebrae 50 (as shown in FIG. 11). In one embodiment, the second abutting surface 32 has at least two second concave arc portions 34. In one example, the second abutting surface 32 has three radially arranged second concave arc portions 34 respectively contacting a triangle area between the vertebral lamina 51 and the spinous process 52 of the vertebrae 50 (as shown in FIG. 11). Similarly, the arc surface of the second abutting surface 32 can be designed according to the radians of patients' vertebral laminas 51. Moreover, the radian of the second abutting surface 32 can be different from the first abutting surface 32.

Referring to FIG. 5 and FIG. 6, in the present embodiment, the second supporting post 33 is a tube structure and can be put around the first supporting post 13. In one embodiment, the cross section of the second supporting post 33 is corresponding to that of the first supporting post 13. An outer surface of the second supporting post 33 includes a convex arc surface 33a and a concave arc surface 33b opposite to each other. The second supporting post 33 has plural second fixing hole 35 and 36. Each of the second fixing holes 35 penetrates from the convex arc surface 33a into the interior of the second supporting post 33, and each of the second fixing holes 35 penetrates from the concave arc surface 33b into the interior of the second supporting post 33. In one example, the second fixing holes 35 and 36 are through holes.

Referring to FIG. 5 and FIG. 6, the sleeve 20 is mainly used to put around the first supporting post 13 and the second supporting post 33, thereby strongly fixing the first supporting member 10 and the second supporting member 30. In the present embodiment, the cross section of the sleeve 20 is corresponding to that of the second supporting post 33. An outer surface of the sleeve 20 includes a convex arc surface 20a and a concave arc surface 20b opposite to each other. In addition, the sleeve 20 has plural first threaded holes 21 and plural second threaded holes 22, in which each of the first threaded holes 21 penetrates from the convex arc surface 20a into the interior of the sleeve 20, and each of the second threaded holes 22 penetrates from the concave arc surface 33b into the interior of the sleeve 20.

Figure 7:
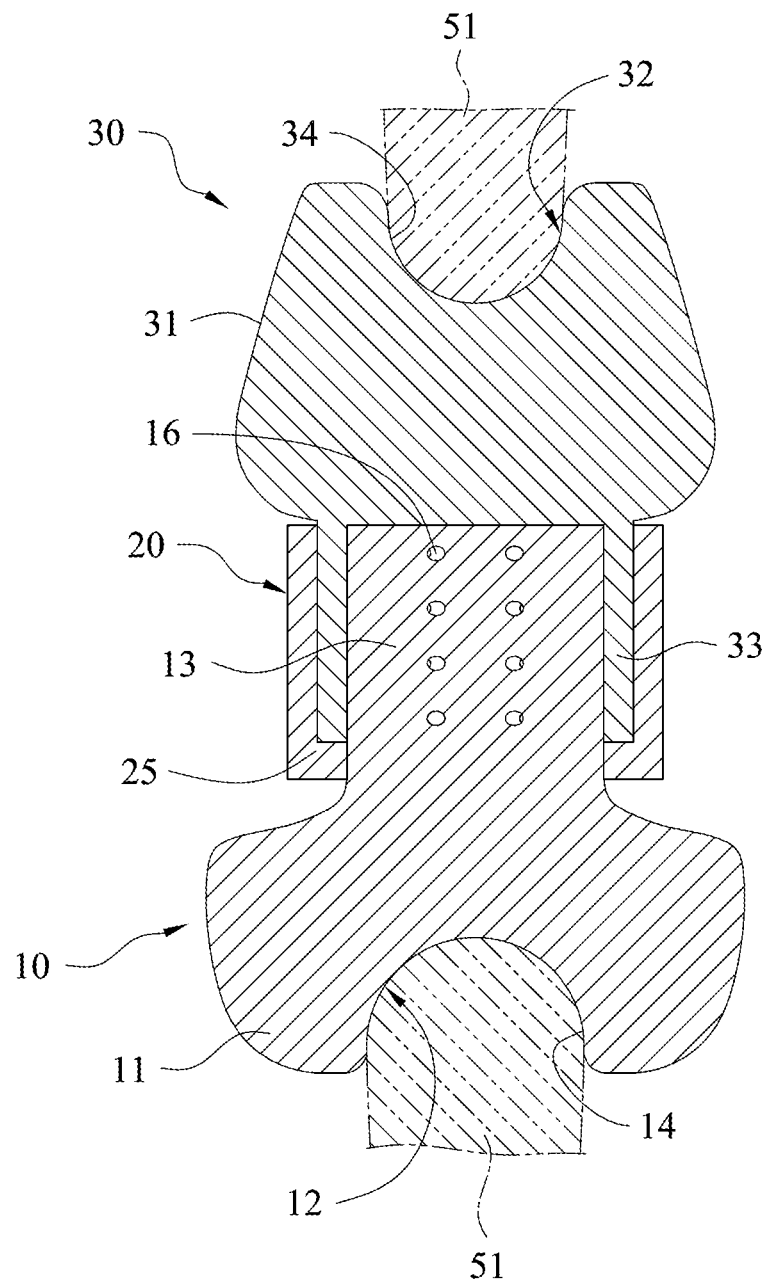
FIG. 7 is a longitudinal-sectional view showing the vertebral lamina supporting device in accordance with the first embodiment of the present invention.

Referring to FIG. 5 and FIG. 7, FIG. 7 is a longitudinal-sectional view showing the vertebral lamina supporting device 100 in accordance with the first embodiment of the present invention. In one embodiment, as shown in FIG. 5, the sleeve 20 has a small opening 23, a large opening 24 and a flange 25. The flange 25 is located on an end edge of the sleeve 20 and surrounds the small opening 23. In the present embodiment, as shown in FIG. 5 and FIG. 7, first supporting post 13 is inserted into the sleeve 20 from the small opening 23, and the second supporting post 33 is inserted into the sleeve 20 from the large opening 24 and is sleeved around the first supporting post 13. In addition, a bottom surface of the second supporting post 33 is contact the flange 25 of the sleeve 20. Therefore, the second supporting member 30 is movable relative to the first supporting member 10 by moving the sleeve 20. In other words, a distance between the second supporting member 30 and the first supporting member 10 can be adjusted by moving the sleeve 20. In the present embodiment, the cross section of the first supporting post 13, the second supporting post 33 and the sleeve 20 are non-circular. Therefore, the first supporting post 13, the second supporting post 33 and the sleeve 20 can only be moved axially relative to each other instead of being moved rotatably relative to each other.

Referring to FIG. 5 and FIG. 6 again, the fixing member 40 is configured to be inserted into and be fixed in the sleeve 20, the second supporting member 30 and the first supporting member 10. In the present embodiment, the fixing member 40 has a threaded portion 41. Therefore, after the fixing member 40 is sequentially inserted into the sleeve 20, the second supporting post 33 and the first supporting post 13, the threaded portion 41 of the fixing member 40 can be screwed on the sleeve 20. Specifically, the fixing member 40 is first sequentially inserted into the first threaded hole 21 of the sleeve 20, the second fixing hole 35 of the second supporting post 33, the opening 16 of the first supporting post 13, the opening 17 of the first supporting post 13, the second fixing hole 36 of the second supporting post 33 and the second threaded hole 22 of the sleeve 20, and then the threaded portion 41 of which is screwed on the second threaded hole 22 of the sleeve 20. In one embodiment, the fixing member 40 further includes a head portion 42, and the head portion 42 and the threaded portion 41 are located on two opposite sides of the fixing member 40. Therefore, when the threaded portion 41 of the fixing member 40 is screwed in the second threaded hole 22, the head portion 42 of the fixing member 40 is located in the first threaded hole 21. In one embodiment, a nut having external thread can be screwed into the first threaded hole 21 to abut against the head portion 42 of the fixing member 40 so as to stably position the fixing member 40.

Figure 1:
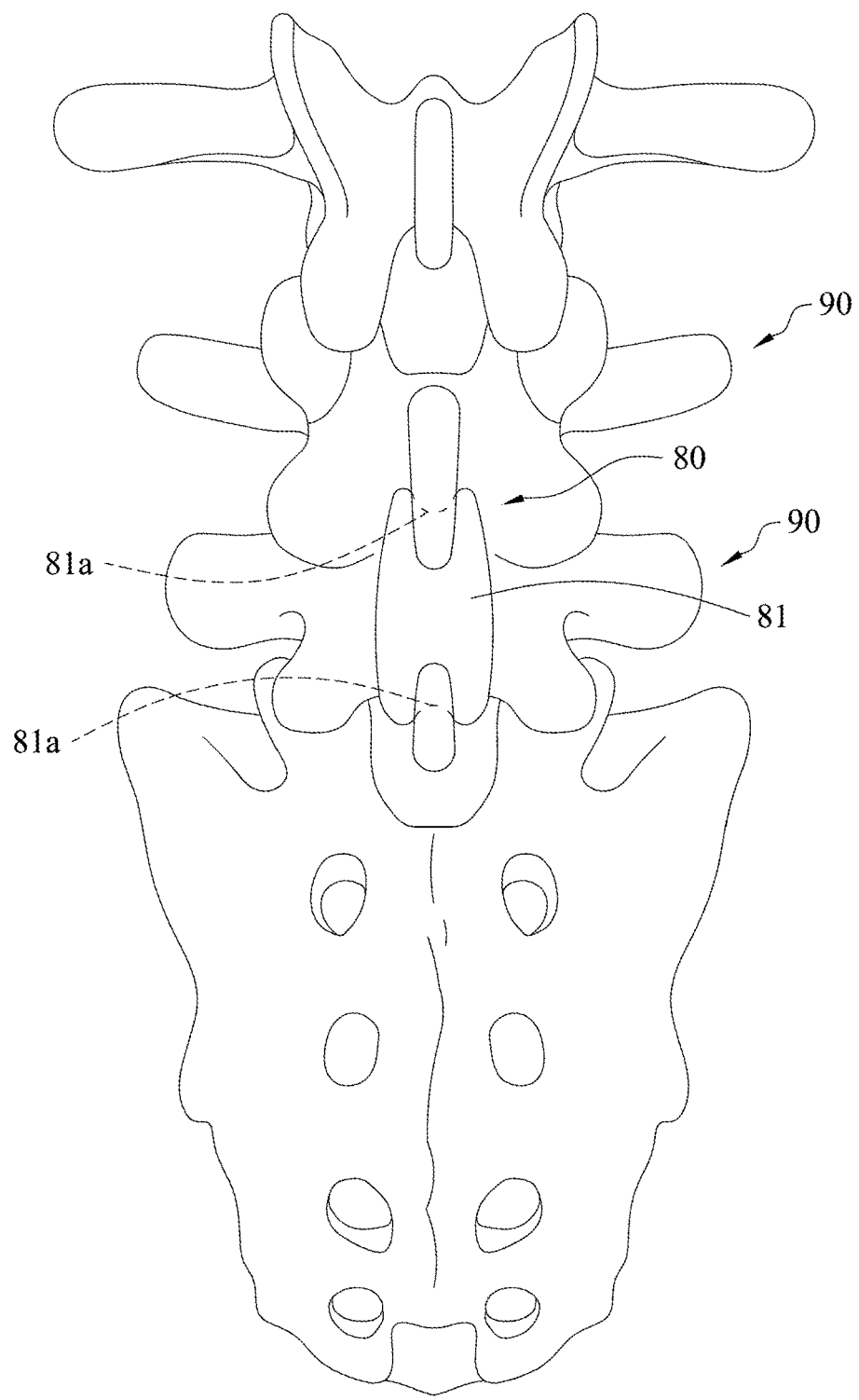
FIG. 1 is a schematic diagram showing a conventional spinous process device in use.
Figure 2:
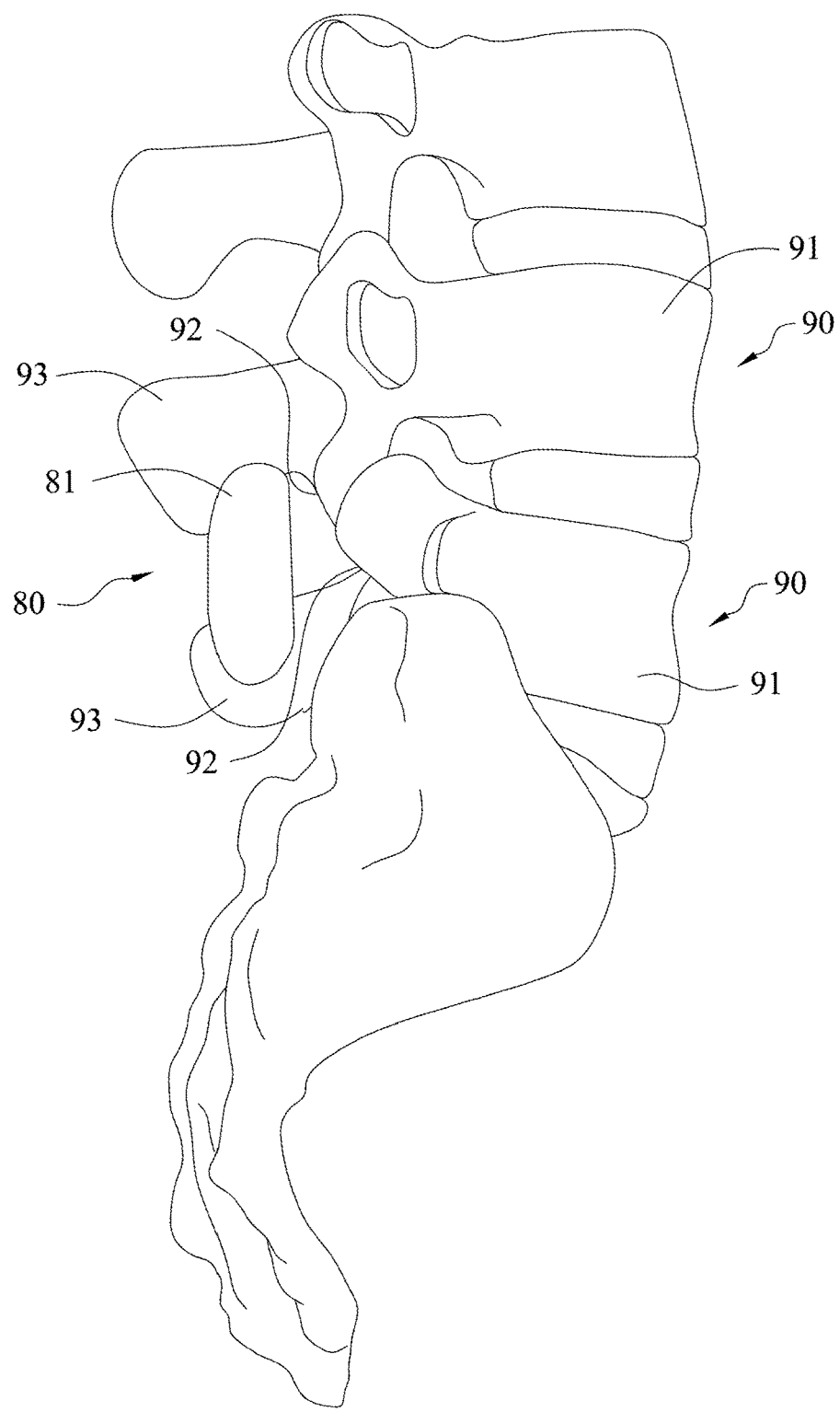
FIG. 2 is another schematic diagram showing the conventional spinous process device in use.
Figure 3:
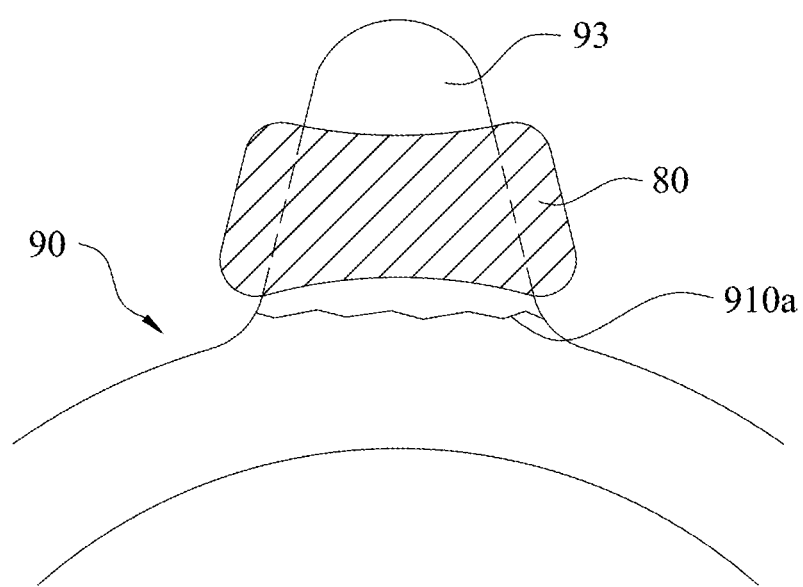
FIG. 3 is a schematic diagram showing a relative position between the vertebrae and the conventional spinous process device.

It is noted that, the number of the fixing member 40 and the way of inserting the fixing member 40 can be varied according to different requirements. As shown in the embodiment of FIG. 3, the number of the fixing member 40 is 2 and the fixing members 40 are intersected with each other. In addition, the sleeve 20 is made of metal, and the first supporting member 10 and the second supporting member 30 are made of lightweight material having elasticity, such as plastics. Therefore, fixing member 40 can be inserted into the first supporting member 10 and the second supporting member 30 and be screwed on the sleeve 20. In some examples, the first supporting base 11 of the first supporting member 10 and the second supporting base 31 of the second supporting member 30 are made of materials different from the sleeve 20.

Figure 8:
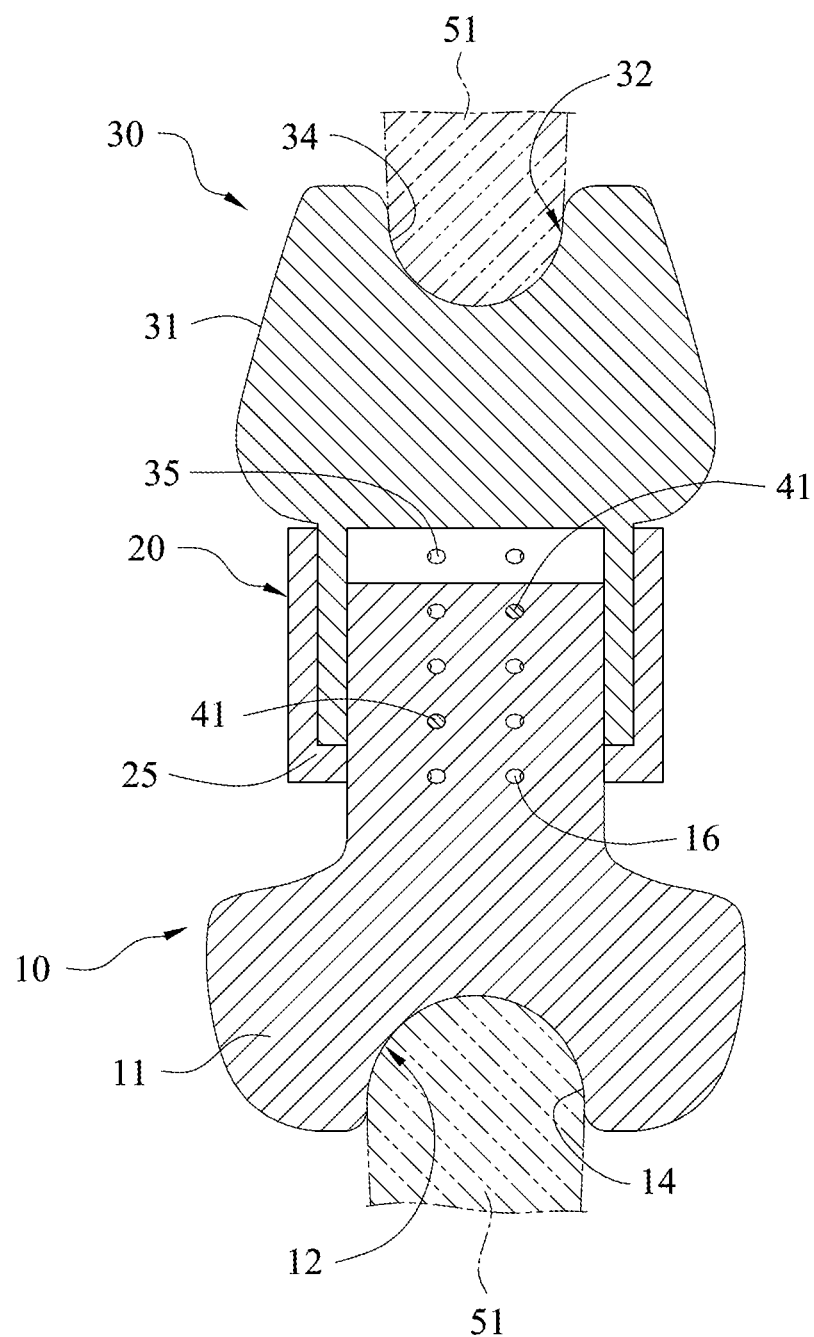
FIG. 8 is a longitudinal-sectional view showing the vertebral lamina supporting device in use in accordance with the first embodiment of the present invention.
Figure 9:
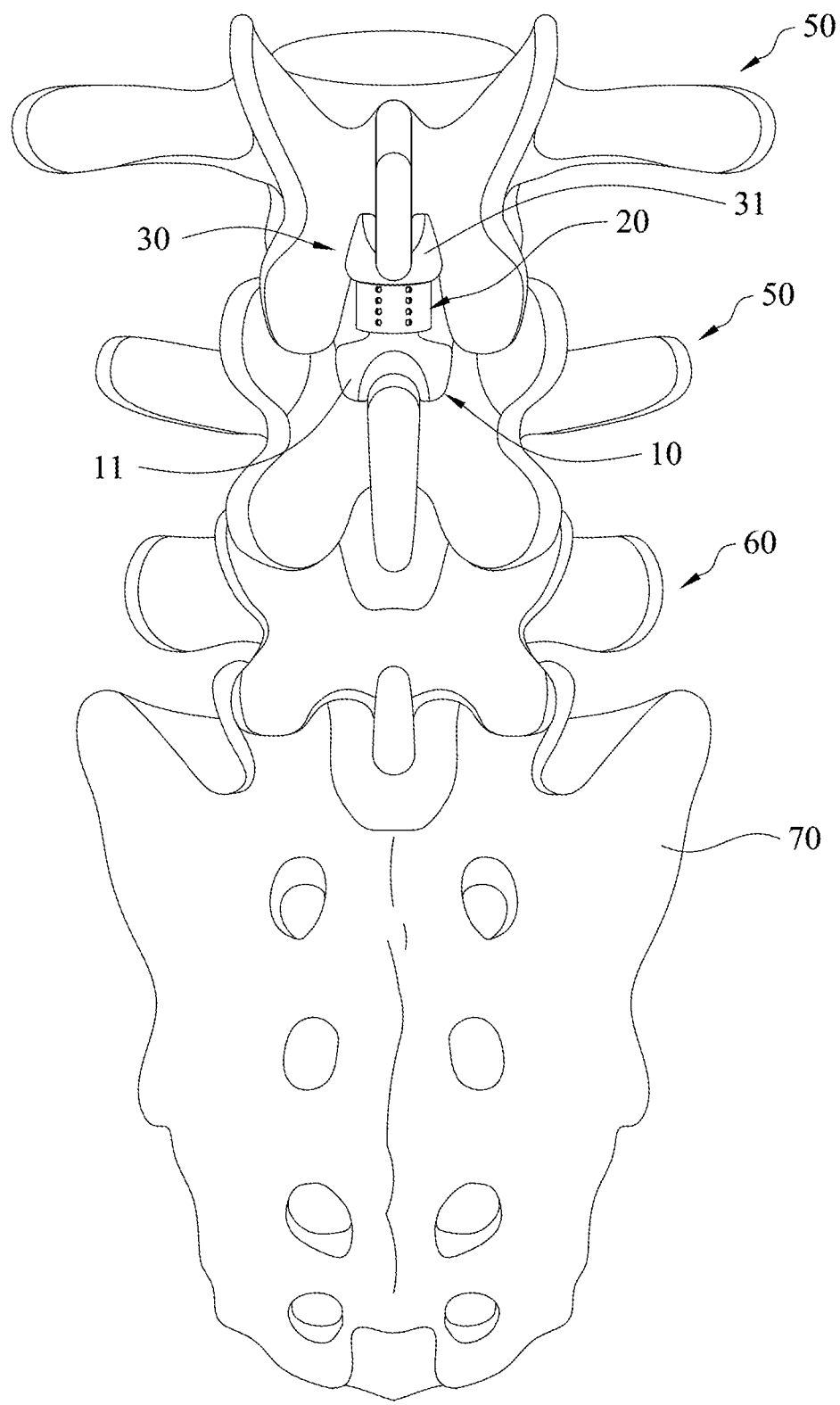
FIG. 9 is a schematic diagram showing the vertebral lamina supporting device in use in accordance with the first embodiment of the present invention.
Figure 10:
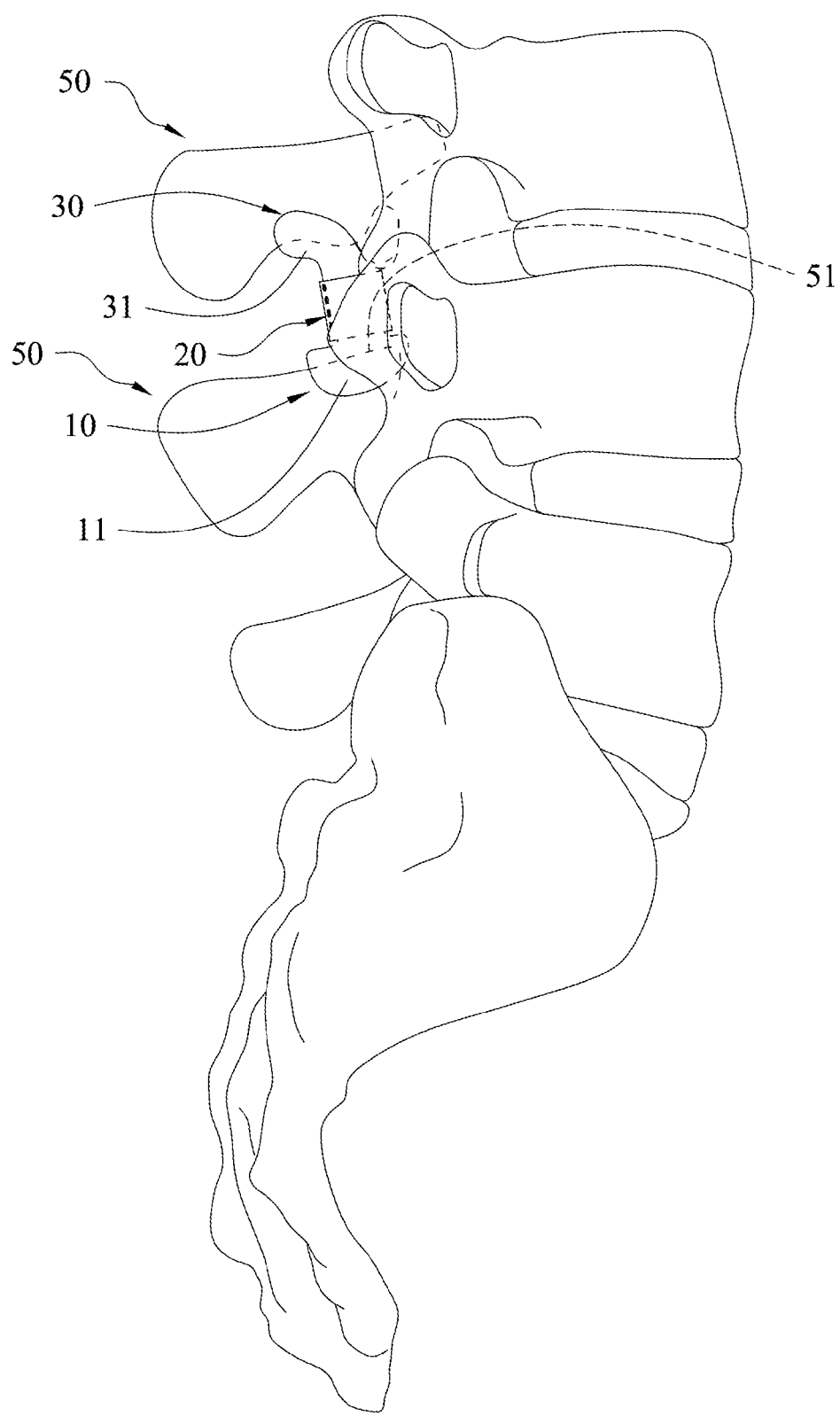
FIG. 10 is another schematic diagram showing the vertebral lamina supporting device in use in accordance with the first embodiment of the present invention.

Operation of using the vertebral lamina supporting device 100 of the present invention is described below. Referring to FIG. 7 to FIG. 10, in which FIG. 8 is a longitudinal-sectional view showing the vertebral lamina supporting device in use in accordance with the first embodiment of the present invention, and FIG. 9 and FIG. 10 are schematic diagrams showing the vertebral lamina supporting device 100 in use in accordance with the first embodiment of the present invention. Firstly, the engaged first supporting member 10, the second supporting member 30 and the sleeve 20 are placed in a space between two adjacent vertebral laminas 51. Thereafter, the sleeve 20 is moved to slide the second supporting member 30 relative to the first supporting member 10 so as to adjust a distance between the first abutting surface 12 and the second abutting surface 32 for suitably supporting two adjacent vertebral laminas 51 of the vertebrae 50. After finishing adjusting the distance between the first abutting surface 12 and the second abutting surface 32, the fixing member 40 is inserted into the sleeve 20, the second supporting member 30 and the first supporting member 10 so as to secure the sleeve 20, the second supporting member 30 and the first supporting member 10.

As shown in FIG. 8 to FIG. 10, the vertebral lamina supporting device 100 is stably disposed between two adjacent vertebral laminas 51 of the vertebrae 50. Moreover, the first abutting surface 12 of the first supporting member 10 and the second abutting surface 32 of the second supporting member 30 respectively abut against the two adjacent vertebral laminas 51 of the vertebrae 50 so that the two adjacent vertebral laminas 51 can be supported by the first supporting member 10 and the second supporting member 30 to prevent the spinous process 52 from being fractured due to the concentrated force applied on the spinous process 52.

It is noted that, because the vertebral lamina supporting device 100 of the present embodiment has the first abutting surface 12 and the second abutting surface 32, the vertebral lamina supporting device 100 can be placed between a vertebral lamina of a lumbar vertebrae 60 and a sacral vertebrae 70. Specifically, the vertebral lamina supporting device 100 can be placed between the spinous processes of the last lumbar vertebrae 60 and the top portion of the sacral vertebrae 70.

Figure 12:
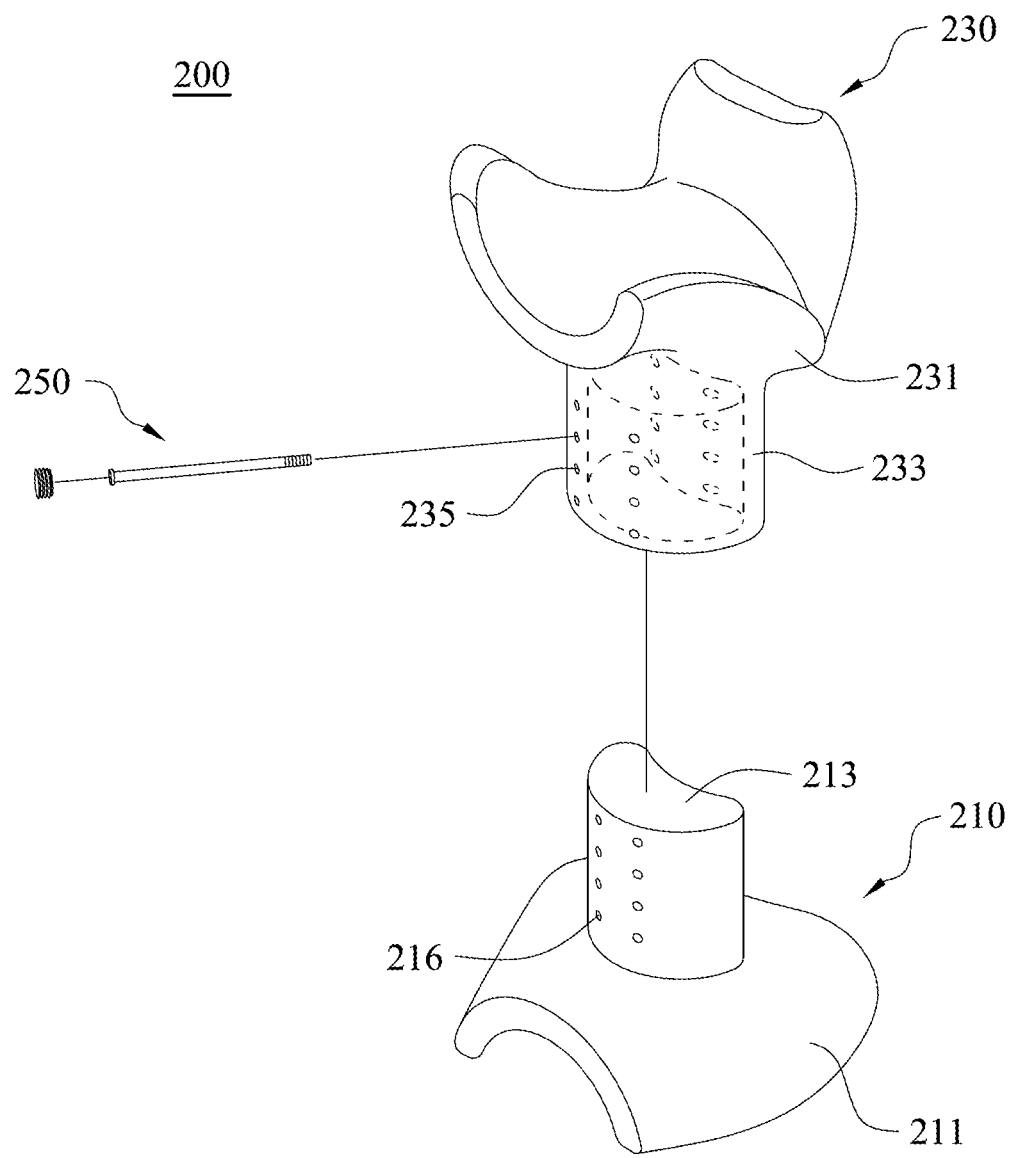
FIG. 12 is a schematic exploded view of a vertebral lamina supporting device in accordance with a second embodiment of the present invention.

Referring to FIG. 12, FIG. 12 is a schematic exploded view of a vertebral lamina supporting device 200 in accordance with a second embodiment of the present invention. A structure of the vertebral lamina supporting device 200 of the present embodiment is similar to that of the aforementioned vertebral lamina supporting device 100, and the main difference therebetween is that the vertebral lamina supporting device 200 does not have the sleeve 20 as shown in FIG. 4. The vertebral lamina supporting device 200 mainly includes a first supporting member 210, a second supporting member 230 and at least one connecting member, in which the connecting member of the present embodiment is a fixing member 250. Therefore, after adjusting a distance between the first supporting member 210 and the second supporting member 230, the fixing member 250 can be used to position the first supporting member 210 and the second supporting member 230.

As shown in FIG. 12, structures of the first supporting member 210, the second supporting member 230 and the fixing member 250 are the same as those of the first supporting member 10, the second supporting member 30 and the fixing member 40, and therefore will not be described again herein. In some embodiments, the first supporting member 210 includes a first supporting base 211 and a first supporting post 213, in which the first supporting post 213 has plural first fixing holes 216. The second supporting member 230 includes a second supporting base 231 and a second supporting post 233, in which the second supporting post 233 has plural second fixing holes 235. In one example, each of the first fixing holes 216 is a through hole, and each of the second fixing holes 235 is a threaded hole. Therefore, the fixing member 250 can be inserted into and be fixed in the first supporting post 213 and the second supporting post 233. In some examples, the first supporting post 211 and the second supporting post 233 are made of metal, thereby increasing the stability of the fixing member 250 disposed therein. The first supporting base 211 and the second supporting base 231 are made of lightweight material having elasticity, such as plastics, so as to increase comfort of the patient when the vertebral lamina supporting device 200 is disposed on the vertebrae.

Figure 13:
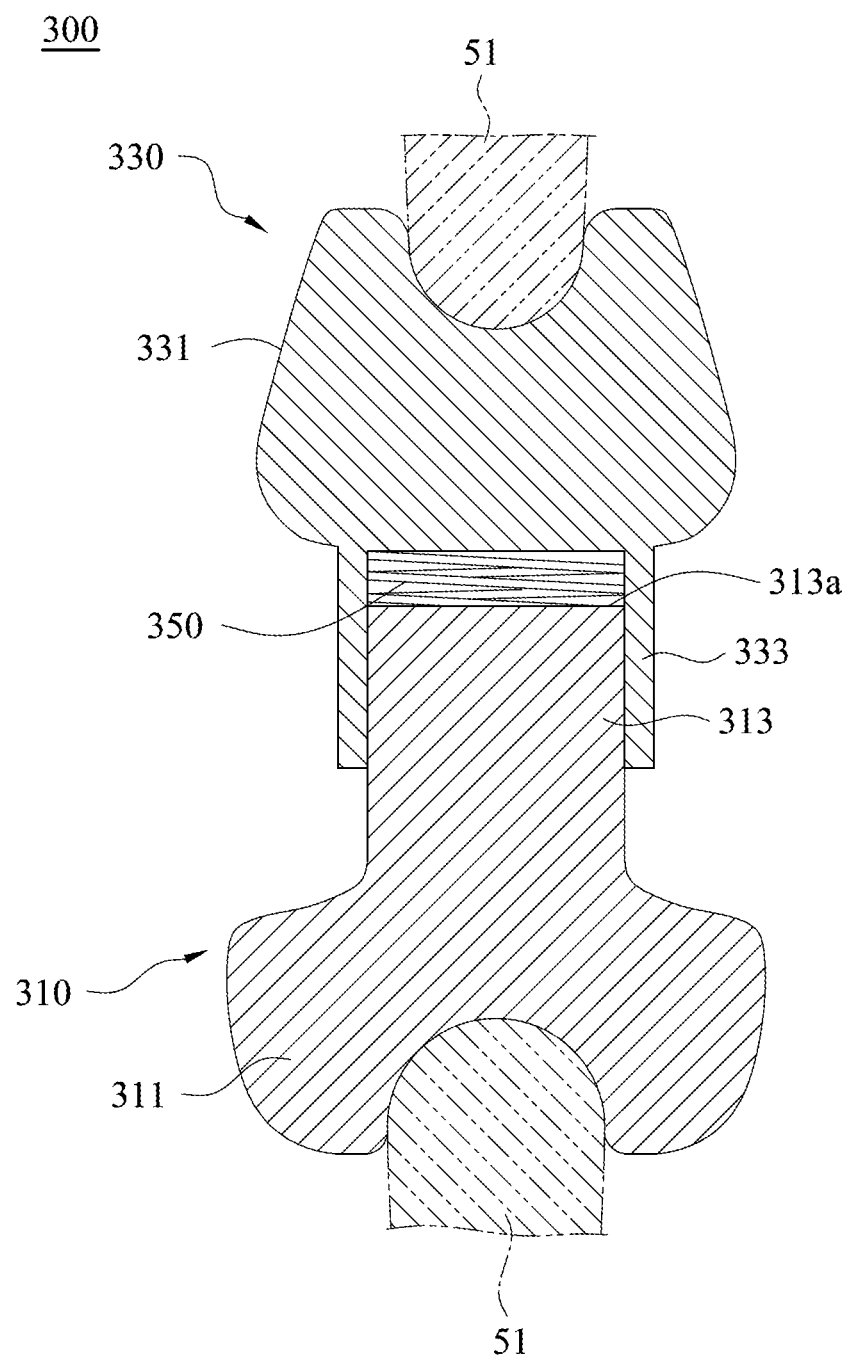
FIG. 13 is a longitudinal-sectional view showing a vertebral lamina supporting device in accordance with a third embodiment of the present invention.
Figure 14:
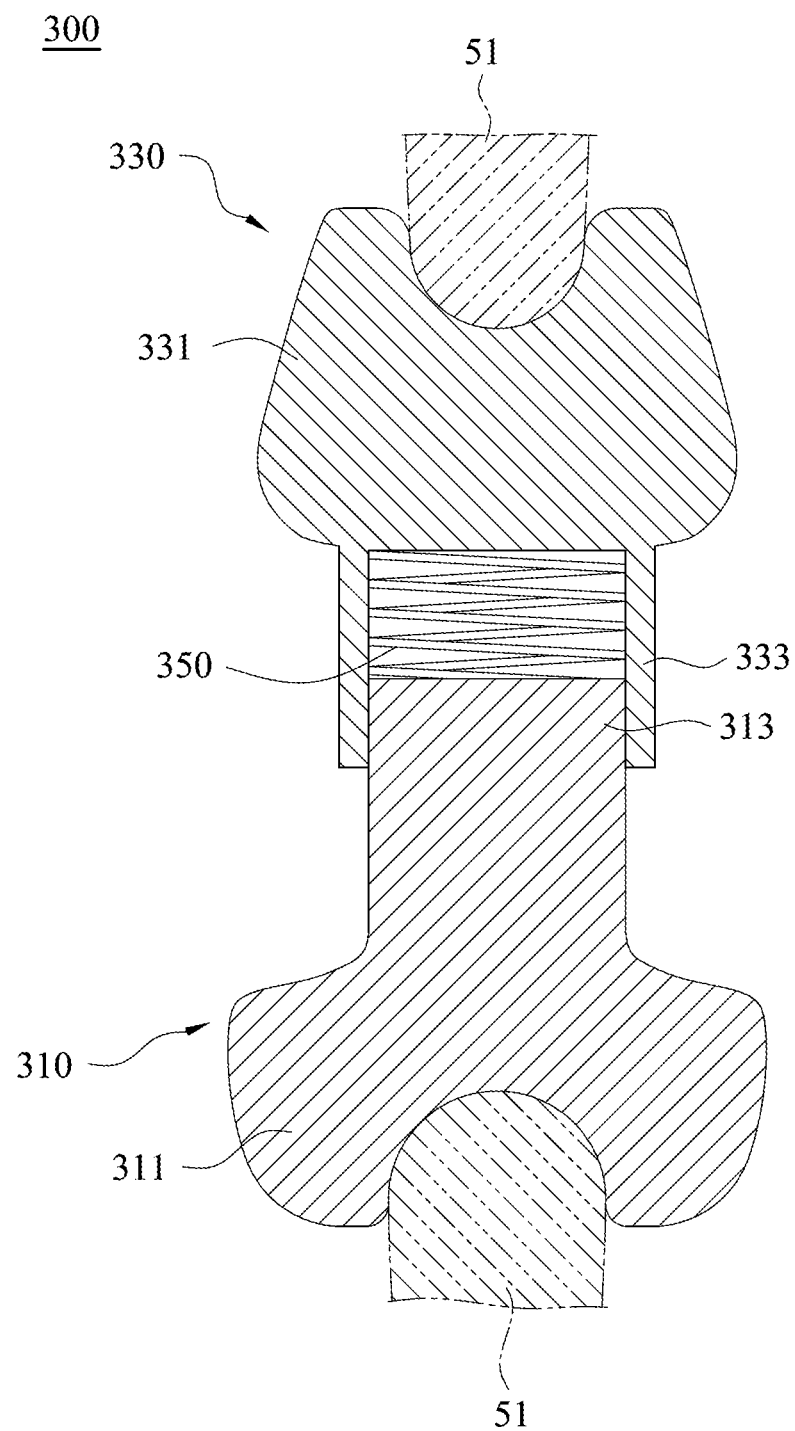
FIG. 14 is another longitudinal-sectional view showing the vertebral lamina supporting device in accordance with the third embodiment of the present invention.

Referring to FIG. 13 and FIG. 14, FIG. 13 and FIG. 14 are longitudinal-sectional views showing a vertebral lamina supporting device 300 in accordance with a third embodiment of the present invention. A structure of the vertebral lamina supporting device 300 of the present embodiment is similar to that of the aforementioned vertebral lamina supporting device 200, and the main difference therebetween is that a connecting member of the vertebral lamina supporting device 300 is an elastic member 350. The vertebral lamina supporting device 300 mainly includes a first supporting member 310, a second supporting member 330 and the connecting member (i.e. the elastic member 350). As shown in FIG. 13, structures of the first supporting member 310 and the second supporting member 330 are the same as those of the first supporting member 10 and the second supporting member 30. In some embodiments, the first supporting member 310 includes a first supporting base 311 and a first supporting post 313, in which the first supporting post 313 is a solid structure. The second supporting member 330 includes a second supporting base 331 and a second supporting post 333, in which the second supporting post 333 is a tube structure and can be put around the first supporting post 313. In the present embodiment, the elastic member 350 is disposed in the second supporting post 333 and abuts against a top surface 313a of the first supporting post 313.

Therefore, before placing the vertebral lamina supporting device 300 between two adjacent vertebral laminas 51, the first supporting member 310 and the second supporting member 330 are moved relative to each other by an application of an external force (as shown in FIG. 13), thereby deforming the elastic member 350. After the vertebral lamina supporting device 300 is placed in a space between two adjacent vertebral laminas 51 and the external force is released, the first supporting member 310 and the second supporting member 330 will move apart from each other by the recovery force of the elastic member 350 (as shown in FIG. 14), so that the first supporting member 310 and the second supporting member 330 can abut against and elastically support the two adjacent vertebral laminas 51. In some embodiments, after the first supporting member 310 and the second supporting member 330 are stably abut against the two adjacent vertebral laminas 51, a fixing member can be used to secure the relative position of the first supporting member 310 and the second supporting member 330, so as to increase the stability of the vertebral lamina supporting device 300.

Figure 15:
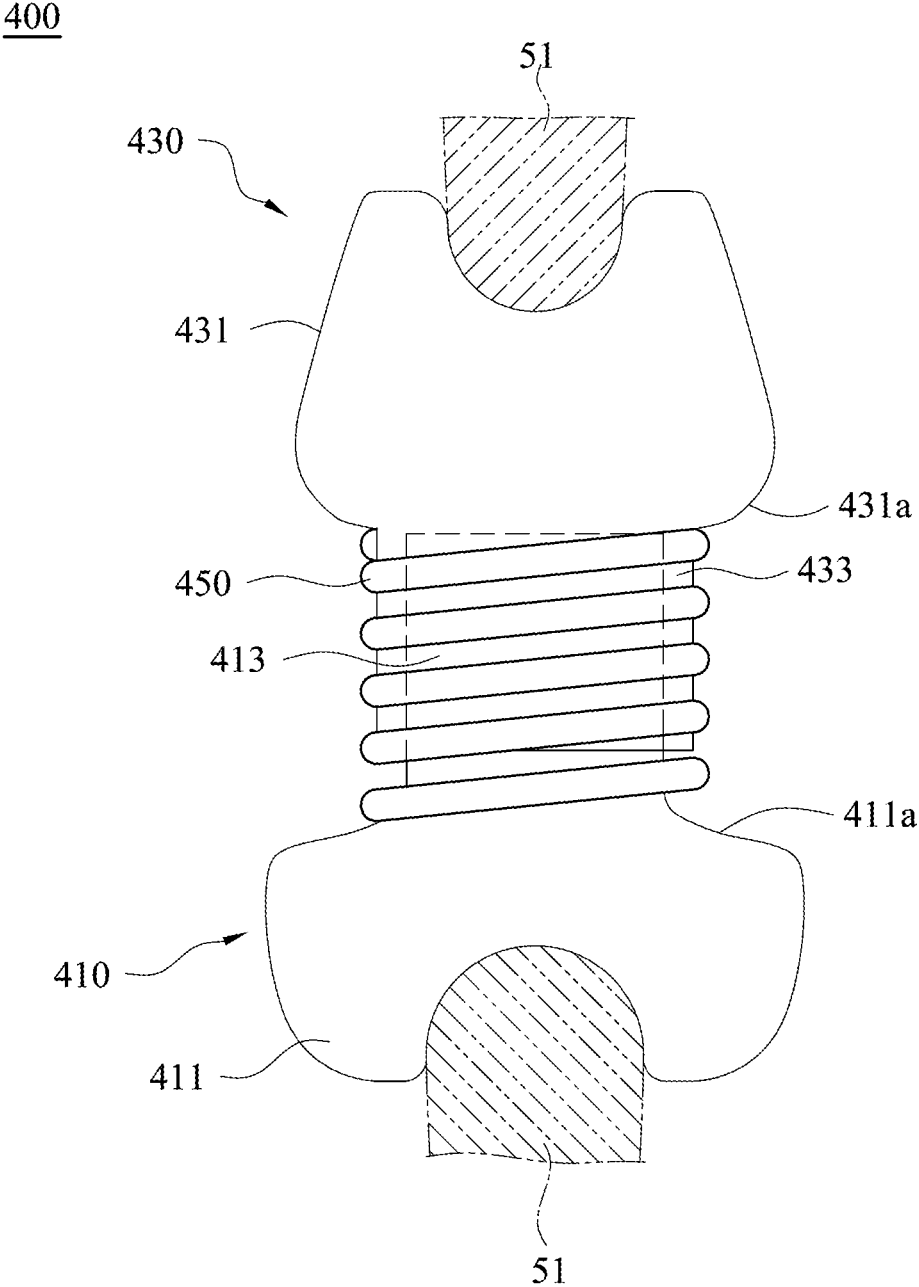
FIG. 15 is a side view showing a vertebral lamina supporting device in accordance with a fourth embodiment of the present invention.
Figure 16:
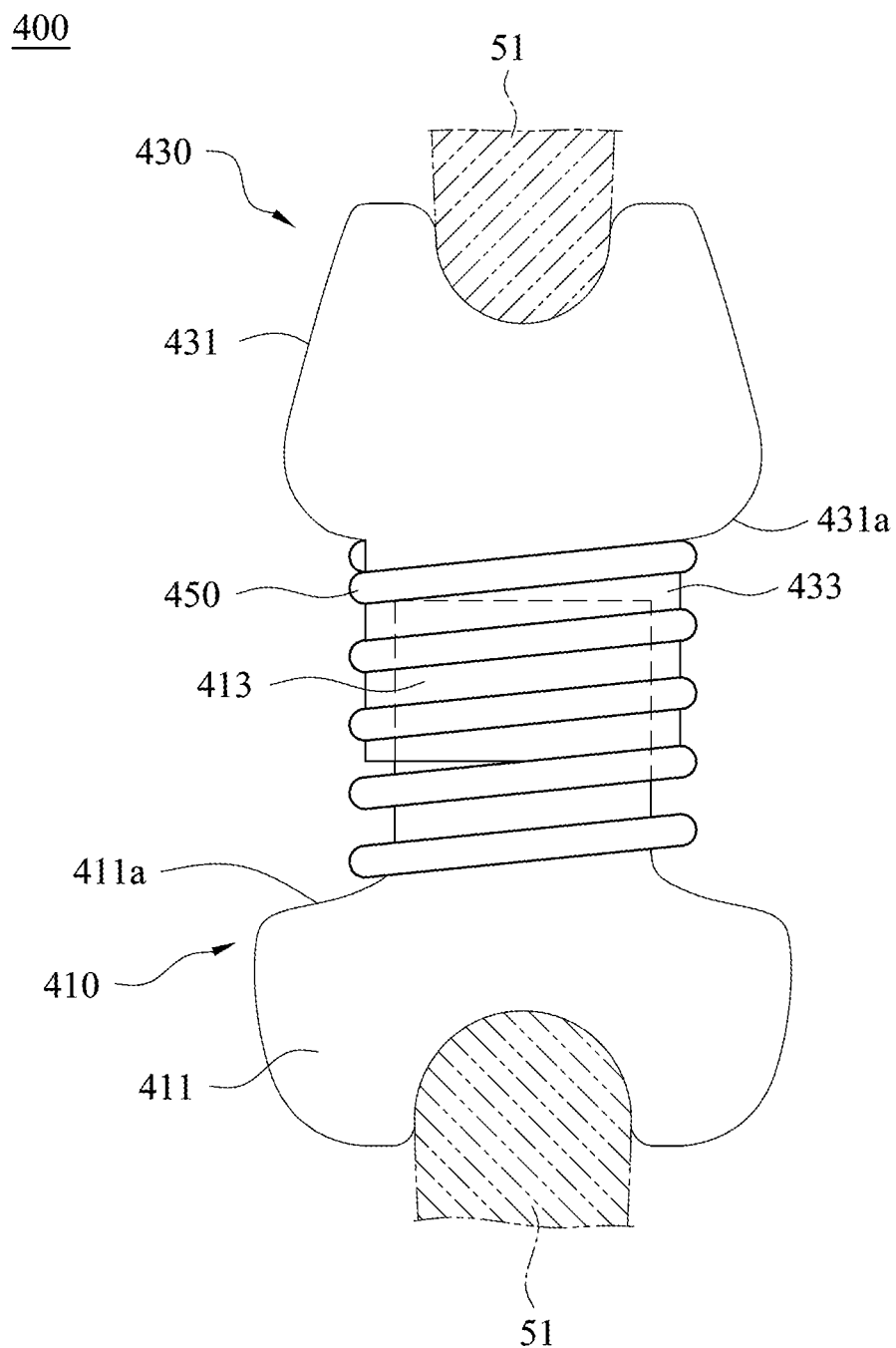
FIG. 16 is another side view showing the vertebral lamina supporting device in accordance with the fourth embodiment of the present invention.

Referring to FIG. 15 and FIG. 16, FIG. 15 and FIG. 16 are different side views showing a vertebral lamina supporting device 400 in accordance with a fourth embodiment of the present invention. A structure of the vertebral lamina supporting device 400 of the present embodiment is similar to that of the aforementioned vertebral lamina supporting device 300. The vertebral lamina supporting device 400 mainly includes a first supporting member 410, a second supporting member 430 and the connecting member (i.e. the elastic member 450). As shown in FIG. 15 and FIG. 16, structures of the first supporting member 410 and the second supporting member 430 are the same as those of the first supporting member 310 and the second supporting member 330. In some embodiments, the first supporting member 410 includes a first supporting base 411 and a first supporting post 413, in which the first supporting post 413 is a solid structure. The second supporting member 430 includes a second supporting base 431 and a second supporting post 433, in which the second supporting post 433 is a tube structure and can be put around the first supporting post 313. In the present embodiment, the first supporting base 411 has a first surface 411a facing the second supporting member 430, and the second supporting base 431 has a second surface 431a facing the first supporting member 410. In the present embodiment, the elastic member 450 surrounds the first supporting post 413 and the second supporting post 433, in which one end of the elastic member 450 abuts against the first surface 411a, and the other end of the elastic member 450 abuts against the second surface 431a.

Therefore, before placing the vertebral lamina supporting device 400 between two adjacent vertebral laminas 51, the first supporting member 410 and the second supporting member 430 are moved relative to each other by an application of an external force (as shown in FIG. 15), thereby deforming the elastic member 450. After the vertebral lamina supporting device 400 is placed in a space between two adjacent vertebral laminas 51 and the external force is released, the first supporting member 410 and the second supporting member 430 will move apart from each other by the recovery force of the elastic member 450 (as shown in FIG. 16), so that the first supporting member 410 and the second supporting member 430 can abut against and elastically support the two adjacent vertebral laminas 51. In some embodiments, after the first supporting member 410 and the second supporting member 430 are stably abut against the two adjacent vertebral laminas 51, a fixing member can be used to secure the relative position of the first supporting member 410 and the second supporting member 430, so as to increase the stability of the vertebral lamina supporting device 400.

Figure 17:
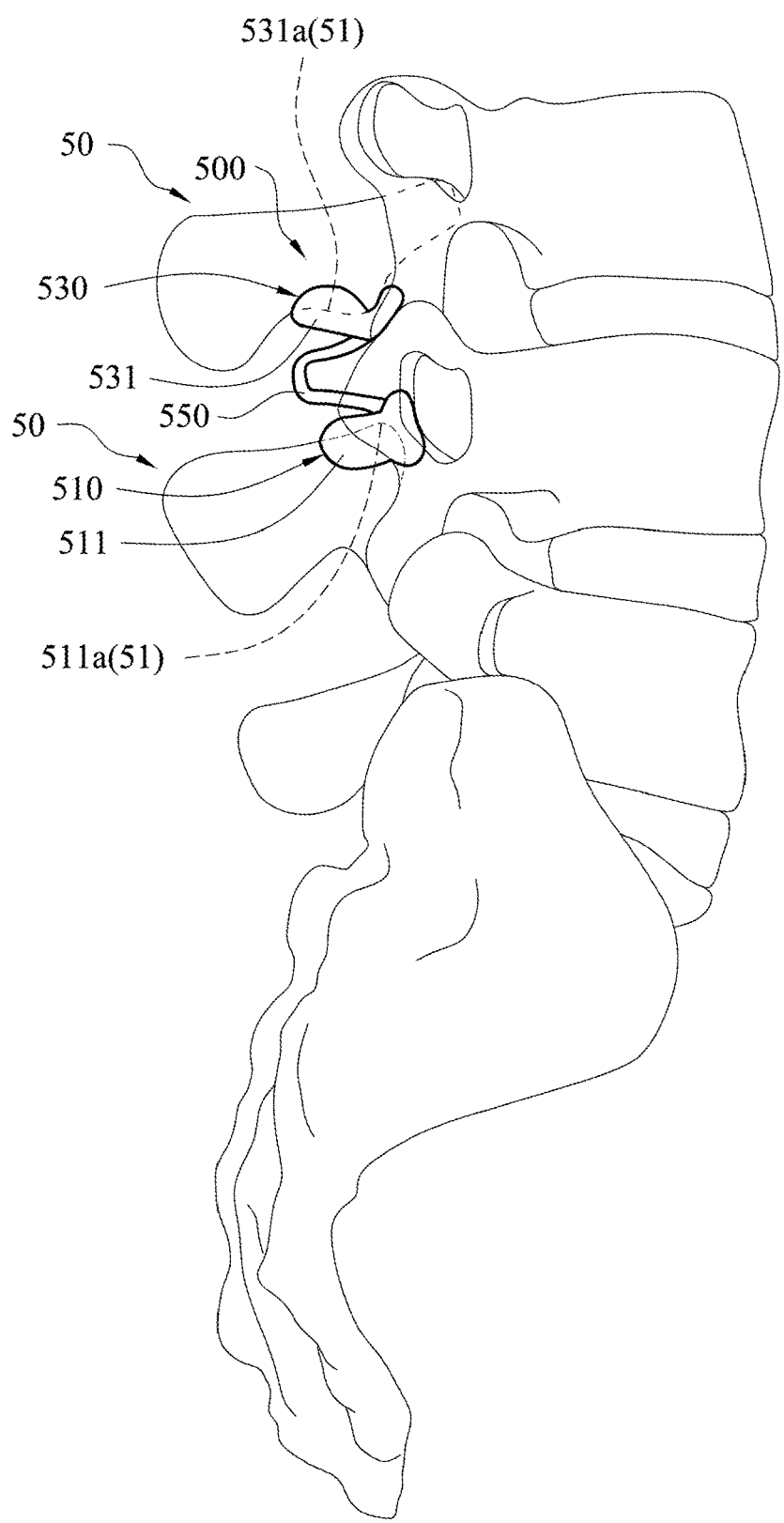
FIG. 17 is a schematic diagram showing a vertebral lamina supporting device in use in accordance with a fifth embodiment of the present invention.

Referring to FIG. 17, FIG. 17 is a schematic diagram showing a vertebral lamina supporting device 500 in use in accordance with a fifth embodiment of the present invention. A structure of the vertebral lamina supporting device 500 of the present embodiment is similar to that of the aforementioned vertebral lamina supporting device 400. The vertebral lamina supporting device 500 mainly includes a first supporting member 510, a second supporting member 530 and the connecting member (i.e. the elastic member 550). In the present embodiment, the elastic member 550 is disposed between the first supporting member 510 and the second supporting member 530. Moreover, the first supporting member 510, the second supporting member 530 and the elastic member 550 are integrally formed. As shown in FIG. 17, the first supporting member 510 includes a first supporting base 511, and the second supporting member 530 includes a second supporting base 531. In the present embodiment, the elastic member 550 is connected between the first supporting base 511 and the second supporting base 531.

Referring to FIG. 17 again, structures of the first supporting base 511 and the second supporting base 531 are similar to those of first supporting base 411 and the second supporting base 431. In some embodiments, the first supporting base 511 has a first abutting surface 511a which is mainly used to abut against the vertebral lamina 51 of the vertebrae 50. In one embodiment, the first abutting surface 511a has at least two first concave arc portions. More specifically, the first abutting surface 511a has three radially arranged first concave arc portions respectively contacting a triangle area between the vertebral lamina 51 and the spinous process 52 of the vertebrae 50 (as shown in FIG. 11). Moreover, the second supporting base 531 has a second abutting surface 531a which is mainly used to abut against the vertebral lamina 51 of the vertebrae 50. In one embodiment, the second abutting surface 531a has at least two second concave arc portions. More specifically, the second abutting surface 531a has three radially arranged first concave arc portions respectively contacting a triangle area between the vertebral lamina 51 and the spinous process 52 of the vertebrae 50 (as shown in FIG. 11). In the present embodiment, the elastic member 550 is a C-shaped structure connected between the first supporting base 511 and the second supporting base 531.

Therefore, before placing the vertebral lamina supporting device 500 between two adjacent vertebral laminas 51, the first supporting member 510 and the second supporting member 530 are moved relative to each other by an application of an external force, thereby deforming the elastic member 550. After the vertebral lamina supporting device 500 is placed in a space between two adjacent vertebral laminas 51 and the external force is released, the first supporting member 510 and the second supporting member 530 will move apart from each other by the recovery force of the elastic member 550, so that the first supporting member 510 and the second supporting member 530 can abut against and elastically support the two adjacent vertebral laminas 51. In some embodiments, after the first supporting member 510 and the second supporting member 530 are stably abut against the two adjacent vertebral laminas 51, the first abutting surface 511a and the second abutting surface 531a can fit the contact surfaces of the adjacent vertebral laminas 51, so as to increase the stability of the vertebral lamina supporting device 500.

According to the aforementioned embodiments of the present invention, the relative position between the first supporting member and the second supporting member can be adjusted to change a gap between the two adjacent vertebrae and to steadily support the two adjacent vertebrae. In addition, each of the first abutting surface and the second abutting surface of the vertebral lamina supporting device has the concave arc surfaces which can abut against the triangle area between the vertebral lamina and the spinous process of the vertebrae, such that the supporting surface is increased, thereby preventing the spinous process from being fractured due to too much force applied on the spinous process.

In addition, the cross section of each of the first supporting member and the second supporting member is in a shape which has a convex side and a concave side opposite to the convex side, and the concave side faces the inner side of the vertebrae, thereby preventing the nerve from being oppressed when the vertebral lamina supporting device is disposed on the vertebrae.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A vertebral lamina supporting device, comprising:
a first supporting member comprising a first supporting base having a first abutting surface and a first surface opposite to the first abutting surface, wherein the first abutting surface has at least three first concave arc portions;
a second supporting member which is movable relative to the first supporting member along a moving direction and comprises a second supporting base having a second abutting surface and a second surface opposite to the second abutting surface, wherein the second abutting surface has at least three second concave arc portions; and
at least one connecting member connected between the first supporting member and the second supporting member;
wherein the at least three first concave arc portions are radially arranged relative to an axis which is parallel to the moving direction, and the at least three first concave arc portions of the first abutting surface are configured to contact a triangle area between a vertebral lamina and a spinous process of a vertebra; and
wherein the at least three second concave arc portions are radially arranged relative to the axis, and the at least three second concave arc portions of the second abutting surface are configured to contact a triangle area between a vertebral lamina and a spinous process of another vertebra.

2. The vertebral lamina supporting device of claim 1, wherein
the first supporting member comprises a first supporting post disposed on the first surface; and
the second supporting member comprises a second supporting post disposed on the second surface.

3. The vertebral lamina supporting device of claim 2, wherein the connecting member is a fixing member which is configured to be inserted into and to be fixed on the first supporting post and the second supporting post.

4. The vertebral lamina supporting device of claim 3, wherein
the first supporting post has at least one first fixing hole;
the second supporting post has at least one second fixing hole corresponding to the first fixing hole; and
the fixing member is inserted into and fixed in the first fixing hole and the second fixing hole.

5. The vertebral lamina supporting device of claim 3, further comprising a sleeve, wherein the sleeve is put around the second supporting post and the first supporting post.

6. The vertebral lamina supporting device of claim 5, wherein
the first supporting post has at least one first fixing hole;
the second supporting post has at least one second fixing hole corresponding to the first fixing hole, and each of the first fixing hole and the second fixing hole is a through hole;
the sleeve has at least one first threaded hole corresponding to the first fixing hole and the second fixing hole; and
the fixing member has a threaded portion, and the fixing member is inserted into the first threaded hole, the second fixing hole and the first fixing hole, and the threaded portion of the fixing member is screwed in the first threaded hole.

7. The vertebral lamina supporting device of claim 6, wherein
the fixing member further comprises a head portion, and the head portion and the threaded portion are respectively disposed on two opposite ends of the fixing member; and
the sleeve further comprises at least one second threaded hole, and the second threaded hole and the first threaded hole are respectively located on two opposite sides of the sleeve, and the head portion is located in the second threaded hole.

8. The vertebral lamina supporting device of claim 7, further comprising at least one nut, wherein the nut is screwed in the second threaded hole and abuts against the head portion of the fixing member.

9. The vertebral lamina supporting device of claim 5, wherein each surface of each of the first supporting post, the second supporting post and the sleeve has a convex arc surface and a concave arc surface.

10. The vertebral lamina supporting device of claim 5, wherein the sleeve has a large opening and a small opening opposite to each other, and the sleeve has a flange surrounding the small opening, wherein a bottom surface of the second supporting post abuts against the flange.

11. The vertebral lamina supporting device of claim 2, wherein the connecting member is an elastic member disposed between the first supporting post and the second supporting post.

12. The vertebral lamina supporting device of claim 11, wherein the elastic member is located in the second supporting post and abuts against a top surface of the first supporting post.

13. The vertebral lamina supporting device of claim 11, wherein the elastic member surrounds the first supporting post and the second supporting post, and one end of the elastic member abuts against the first surface of the first supporting base, and the other end of the elastic member abuts against the second surface of the second supporting base.

14. The vertebral lamina supporting device of claim 1, wherein the connecting member is an elastic member disposed between the first supporting member and the second supporting member.

15. The vertebral lamina supporting device of claim 14, wherein the first supporting member, the second supporting member and the connecting member are integrally formed.

16. The vertebral lamina supporting device of claim 14, wherein the elastic member is a C-shaped structure.

* * * * *